(12) United States Patent
Lee

(10) Patent No.: US 10,179,036 B2
(45) Date of Patent: Jan. 15, 2019

(54) VARIABLE CROSS-SECTIONED ORTHODONTIC ARCHWIRE EQUIPPED WITH INTEGRATED HOOK

(71) Applicant: Jong Ho Lee, Pohang-si (KR)

(72) Inventor: Jong Ho Lee, Pohang-si (KR)

( * ) Notice: Subject to any disclaimer, the term of this patent is extended or adjusted under 35 U.S.C. 154(b) by 0 days.

(21) Appl. No.: 15/946,984

(22) Filed: Apr. 6, 2018

(65) Prior Publication Data

US 2018/0221112 A1 Aug. 9, 2018

Related U.S. Application Data

(63) Continuation of application No. 15/317,152, filed as application No. PCT/KR2015/012398 on Nov. 18, 2015, now abandoned.

(30) Foreign Application Priority Data

Jul. 7, 2015 (KR) .................. 10-2015-0096277

(51) Int. Cl.
| | |
|---|---|
| *A61C 3/00* | (2006.01) |
| *A61C 7/22* | (2006.01) |
| *A61C 7/20* | (2006.01) |
| *A61C 7/28* | (2006.01) |

(52) U.S. Cl.
CPC .................. *A61C 7/22* (2013.01); *A61C 7/20* (2013.01); *A61C 7/28* (2013.01)

(58) Field of Classification Search
CPC ................. A61C 7/20; A61C 7/22; A61C 7/28
USPC .................................................... 433/20, 22
See application file for complete search history.

(56) References Cited

U.S. PATENT DOCUMENTS

| | | | | |
|---|---|---|---|---|
| 1,014,028 A | * | 1/1912 | Angle | A61C 7/285 |
| | | | | 29/896.11 |
| 4,412,819 A | * | 11/1983 | Cannon | A61C 7/20 |
| | | | | 433/20 |
| 4,479,779 A | | 10/1984 | Wool | |
| 4,525,143 A | * | 6/1985 | Adams | A61C 7/12 |
| | | | | 433/5 |
| 5,238,404 A | * | 8/1993 | Andreiko | A61C 7/12 |
| | | | | 433/20 |
| 5,259,760 A | * | 11/1993 | Orikasa | A61C 7/20 |
| | | | | 433/20 |

(Continued)

FOREIGN PATENT DOCUMENTS

| | | |
|---|---|---|
| EP | 2736444 | 6/2014 |
| JP | 06-034607 U | 5/1994 |

(Continued)

OTHER PUBLICATIONS

Chahine, G. et al., "The design and production of Ti6Al4V ELI customized dental implants", The Journal of the Minerals, Metals & Materials Society, Nov. 13, 2008, vol. 60, Issue 11, pp. 50-55.

*Primary Examiner* — Nicholas Lucchesi

(74) *Attorney, Agent, or Firm* — Lee & Associates, LLC

(57) ABSTRACT

Disclosed is an archwire with a varied cross section which is formed integrally with a hook. The archwire includes a customized archwire body corresponding to a setup model of patient's teeth, and the hook which is formed integrally with the archwire body. The archwire body is formed in such a way that at least one region has a cross section different from that of another region.

4 Claims, 11 Drawing Sheets

(56) References Cited

U.S. PATENT DOCUMENTS

| | | | | |
|---|---|---|---|---|
| 5,380,197 | A * | 1/1995 | Hanson | A61C 7/20 433/18 |
| 6,928,733 | B2 * | 8/2005 | Rubbert | A61C 7/20 29/407.04 |
| 2004/0013994 | A1 * | 1/2004 | Goldberg | A61C 7/14 433/8 |
| 2008/0118885 | A1 * | 5/2008 | Devincenzo | A61C 7/00 433/10 |
| 2008/0294260 | A1 * | 11/2008 | Gray | A61F 2/4455 623/17.16 |
| 2009/0061377 | A1 * | 3/2009 | Cope | A61C 7/00 433/18 |
| 2010/0190128 | A1 * | 7/2010 | Wool | A61C 7/20 433/20 |
| 2010/0304321 | A1 | 12/2010 | Patel | |
| 2012/0208144 | A1 * | 8/2012 | Chiaramonte | A61C 7/20 433/20 |
| 2016/0278883 | A1 * | 9/2016 | Fasci | A61C 7/20 |

FOREIGN PATENT DOCUMENTS

| | | |
|---|---|---|
| JP | 03-067787 U | 1/2000 |
| JP | 2001-198143 A | 7/2001 |
| KR | 10-0692646 | 3/2007 |
| KR | 10-1202217 | 11/2012 |

* cited by examiner

FIG. 8A
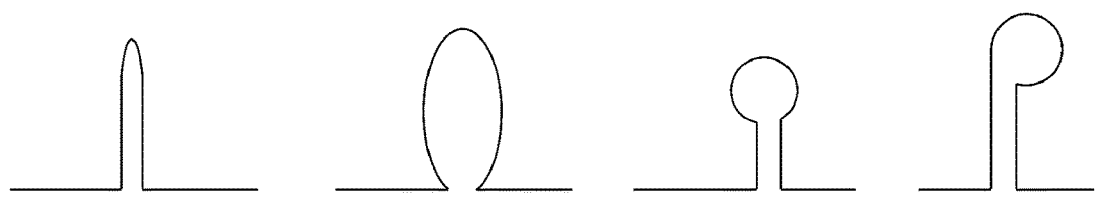
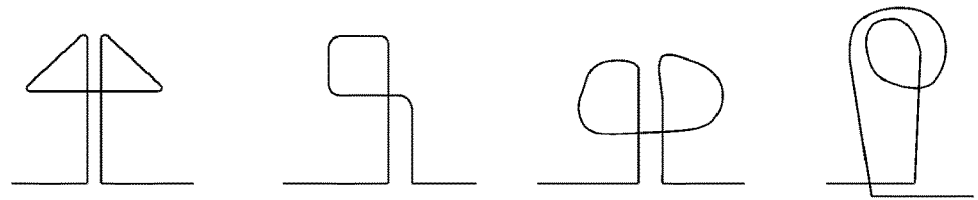
FIG. 8B

VARIABLE CROSS-SECTIONED ORTHODONTIC ARCHWIRE EQUIPPED WITH INTEGRATED HOOK

CROSS-REFERENCE TO RELATED APPLICATIONS

This patent application is a continuation of U.S. patent application Ser. No. 15/317,152 filed on Jan. 8, 2017, which is a national stage application of International Patent Application No. PCT/KR2015/012398 filed on Nov. 18, 2015, which claims priority to Korean Patent Application No. 10-2015-0096277 filed on Jul. 7, 2015, the entire contents of which are incorporated by reference herein.

TECHNICAL FIELD

The present invention relates to an orthodontic archwire. More particularly, the present invention relates to a customized archwire for loop or sliding technique.

BACKGROUND

In general, orthodontic therapy is to straighten crooked teeth by bonding brackets to the teeth and placing and ligating an archwire to slots of the brackets, wherein the teeth are corrected by retracting the teeth using a restoring force of the archwire or controlling torque of the archwire.

A method for retracting six anterior teeth usually employs a loop technique or a sliding technique.

The loop technique includes bending a portion of an archwire to form loops, ligating the archwire to brackets, and anchoring the hooks to the brackets by a ligating wire to produce a retraction force.

FIG. 1 is a view illustrating a process of forming a loop according to the related art.

Referring to FIG. 1, a loop 1' is formed by bending a portion of a wire 1 using a tool. If necessary, a wire hook 2 may be mounted to a portion of the wire beside the loop 1'.

And then, as illustrated in FIGS. 2A, 2B and 2C, the wire is ligated to brackets 4 bonded to patient's teeth.

Finally, the hook 2 is ligated to the brackets by other ligating wire 3.

FIG. 2A shows an early stage before the loop 1' starts activation, and FIG. 2B shows an advanced stage in which retraction of the teeth is completed.

If the activation is completed, the loop 1' is supposed to be disposed at a center of both brackets. Actually, if the teeth are retracted by about 2 mm, the hook 2 abuts against the bracket 4, so that the hook is not further retracted. As a result, the hook 2 already mounted should be removed from the wire, and a new hook should be mounted onto the wire beside the loop.

FIG. 2C shows a new stage in which activation starts again after the hook 2 is mounted onto the wire.

The wire hook 2 is commonly used even in the case of retracting the teeth by the sliding technique.

The sliding technique includes ligating an orthodontic archwire to brackets and linking a closed coil spring or an elastic power chain to a hook to produce a retraction force.

FIG. 3 shows a process of mounting a wire hook according to the related art.

Referring to FIG. 3, a hook 2 is mounted to a proper location of the archwire 1, and a closed coil spring is linked to the hook 2 to produce a traction force.

Since the hook is mounted to the archwire by hands, the degree of precision is lowered. In particular, since a lower end of the hook is fastened to the wire, there is a drawback in that a volume of the archwire is significantly increased.

In particular, the above drawback is remarkable in the case of lingual orthodontic treatment in which a space is limited.

SUMMARY

Accordingly, the present invention has been made in view of the above-mentioned problems occurring in the related art, and an object of the present invention is to provide an archwire which is formed integrally with hooks.

Another object of the present invention is to provide an archwire with a varied cross-sectional structure along a region to maximize conformance of a retraction wire.

The other object of the present invention is to provide an archwire capable of being customized by determining dimensions and kinds of a loop and a hook from coordinates of a space, from which a tooth is extracted, and bracket bonding locations which are figured out in advance from a setup model of patient's teeth.

To accomplish the above-mentioned objects, according to one aspect of the present invention, there is provided an archwire with a varied cross section which is formed integrally with a hook, the archwire including: a customized archwire body corresponding to a setup model of patient's teeth; and the hook which protrudes from one side of the archwire body.

The hook is formed integrally with the archwire body, and the archwire body is formed in such a way that at least one region has a cross section different from that of other region.

Preferably, the hook has a width which is equal to or smaller than that of a slot of a bracket.

The archwire body may be formed integrally with a loop.

A cross-sectional area of the loop is variably determined corresponding to the setup model of the patient's teeth, and an interval between the loop and the hook is preferably within 2 mm.

In the archwire with the varied cross section which is formed integrally with the hook according to the present invention, a location of each bracket is figured out from the setup model of the patient's teeth. The shape of the archwire is obtained from the data, and then a plate is formed to fabricate the archwire.

As a result, the loop, the hook and the archwire are flush with each other by forming a plate. In this instance, the customized archwire with the varied cross section is fabricated by bending the loop at about 70 to 90 degrees according to an oral cavity condition of the patient.

In order to improve conformance of a retraction wire, a cross-sectional area of a posterior wire region of the archwire body may be configured to be larger than that of an anterior wire region.

An inter-bracket region of the archwire body may have a cross-sectional area smaller than that of a portion which is ligated to the slot of the bracket.

The archwire body may be formed integrally with a stop.

The stop may further protrude from the slot of the bracket as the archwire body is ligated to the slot of the bracket.

A portion of the stop protruding from the slot preferably has a T-shape, and one or more stops may be provided which protrude from the slots of the brackets for central incisor, lateral incisor or canine teeth.

The stop is fixed by a ligating wire, and serves to limit horizontally sliding movement of the archwire body in the slot of the bracket.

Preferably, the archwire is made from Ti6Al4V-ELI material.

With the above configuration of according to the present invention, since the cross-sectional area or cross-sectional shape of the archwire is varied along the region, there is provided the archwire formed integrally with the loop, the hook or the stop.

Therefore, the customized archwire can be fabricated only by easily determining the thickness, the length and the kind of the loop and the hook based on bracket bonding positions which are figured out from the setup model of the patient's teeth, and coordinates of a tooth extracting space.

Further, it is possible to solve a problem of loop technique in that since the hook abuts against the bracket, teeth cannot be further retracted, and to prevent the archwire from being released from the slot.

BRIEF DESCRIPTION OF THE DRAWINGS

FIGS. 8A and 8B are views illustrating examples of loops which can be applied to the present invention and cannot be applied to the present invention.

DETAILED DESCRIPTION OF THE DISCLOSURE

Hereinafter, preferred embodiments of the present invention will now be described in detail with reference to the attached drawings, in which like reference numbers denote corresponding parts throughout the drawings.

The terms "comprising" and "including" in the discussion directed to the present invention and the claims are used in an open-ended fashion and thus should be interrupted to mean "including", but not limited thereto.

An orthodontic archwire with a varied cross section which is formed integrally with hooks according to the present invention has a cross section varied along a region, contrary to an orthodontic archwire according to the related art.

For example, a loop, a hook or a stop can be formed by reducing a cross-sectional area of an inter-bracket region or varying a cross section of a desired region.

In addition, the cross-sectional area can be varied by dividing the wire into an anterior region and a posterior region.

To this end, since a location of a bracket ligating portion should be determined in advance, the present invention can be applied to a customized orthodontic appliance. Preferably, the archwire according to the present invention is ligated to a customized bracket.

The orthodontic archwire with the varied cross section according to the present invention is formed integrally with at least one hook. Preferably, the orthodontic archwire has a rectangular wire of a rectangular cross-sectional structure, but a shape of the cross section of the archwire is varied along a region.

The orthodontic archwire with a varied cross section which is formed integrally with hooks according to the present invention will now be described in detail with reference to FIGS. 4 to 8.

Figure 1:
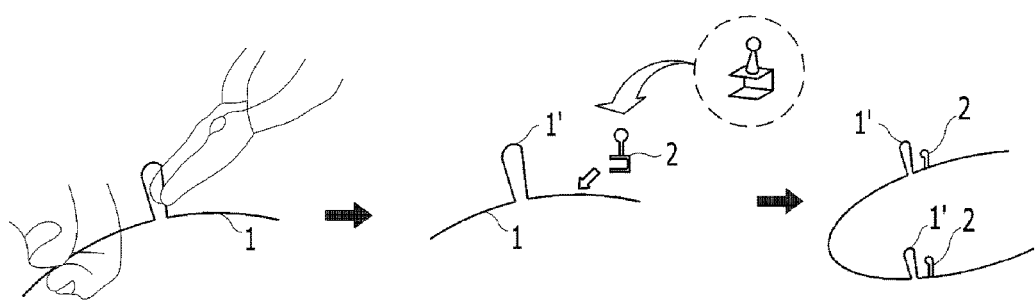
FIG. 1 is a view illustrating a process of forming a loop according to the related art.
Figure 2A:
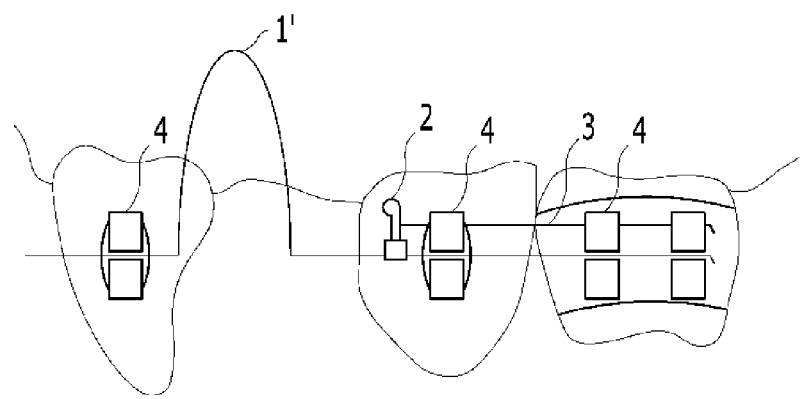
FIGS. 2A, 2B and 2C are views illustrating a process of activating the loop according to the related art and a drawback thereof
Figure 2B:
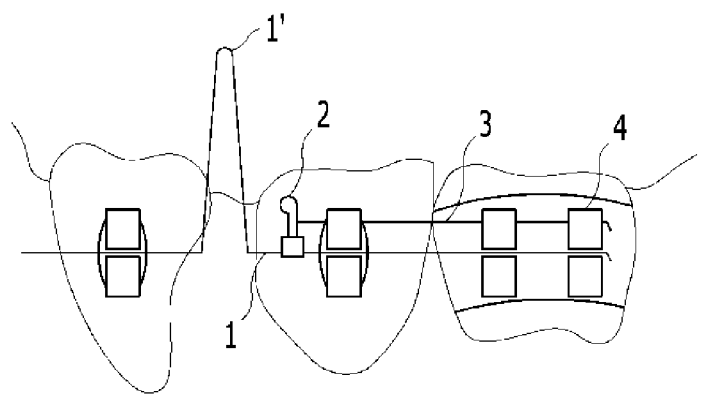
Figure 2C:
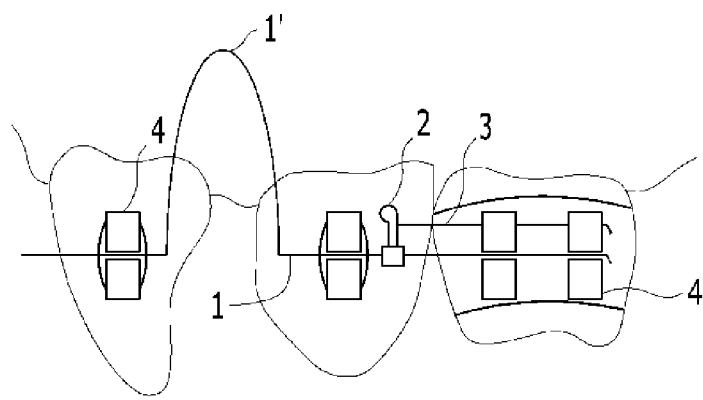
Figure 3:
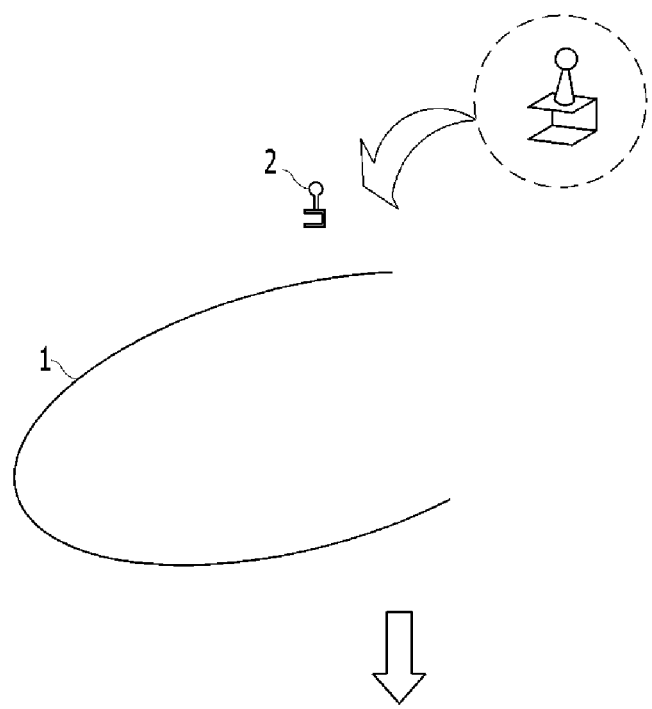
FIG. 3 is a view illustrating a process of mounting a wire hook according to the related art.
Figure 3:
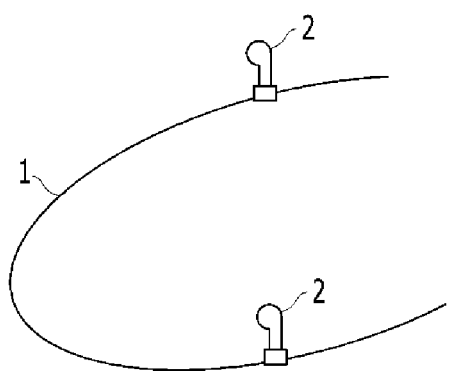
Figure 4:
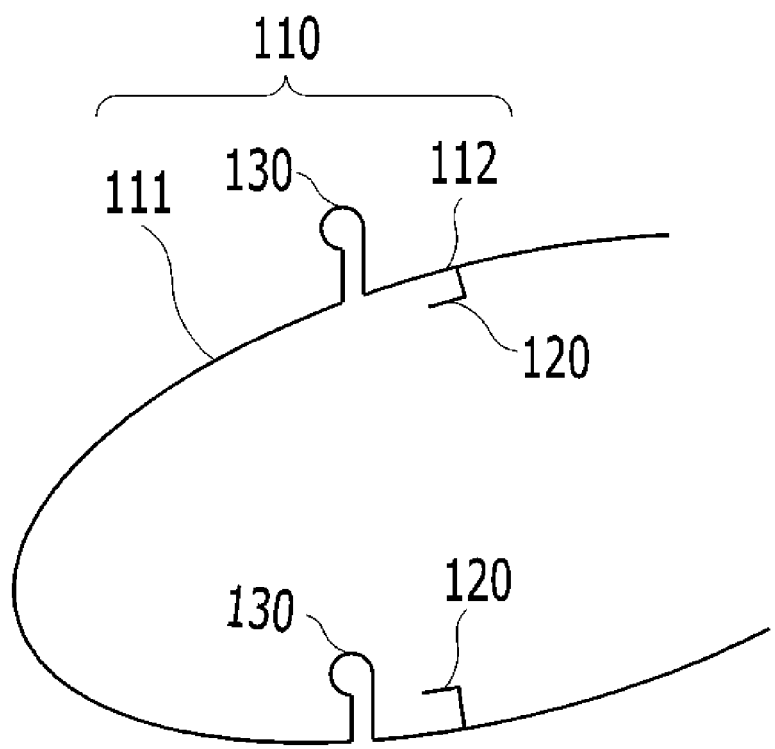
FIG. 4 is a view schematically illustrating an archwire with a varied cross section which is formed integrally with hooks according to one embodiment of the present invention.

FIG. 4 is a view schematically illustrating the archwire with the varied cross section which is formed integrally with hooks according to one embodiment of the present invention.

The embodiment of the present invention is provided with an integral loop which is further formed within a desired distance from the hook, and can be applied to loop technique.

Referring to FIG. 4, the archwire with the varied cross section which is formed integrally with the hooks according to the embodiment of the present invention at least one hook 120 and at least one loop 130 which are formed integrally with an archwire body 110.

The embodiment shown in FIG. 4 relates to a customized archwire which is fabricated in view of a position of a bracket for each tooth or the like, in particular, an archwire for lingual orthodontic treatment when seen from the hook 120 facing an internal direction.

The orientation of the hook 120 is not limited, and, of course, the embodiment can be used as an archwire for buccolingual orthodontic treatment since the hook faces an external direction.

The location of the loop 130 is determined according to a location of a tooth extracting space of a patient.

In the embodiment in FIG. 4, a pair of loops 130 and a pair of hooks 120 are provided to be opposite to each other, but the locations are illustrated to help interesting. The hook 120 and the loop 130 can be provided at only one side, or the location can be changed, according to whether a tooth is extracted or not, or a location where a tooth is extracted.

Preferably, the loop 130 is formed in front of the tooth extracting space. If the loop is activated to retract the teeth, the tooth extracting space is closed. The loop 130 is positioned at the center between both brackets 4.

Figure 7A:
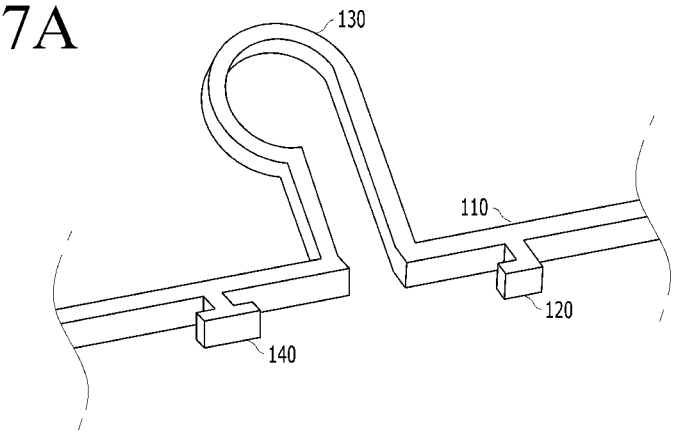
FIGS. 7A and 7B are enlarged views illustrating the archwire in FIG. 4 which is ligated to a slot of a bracket.
Figure 7B:
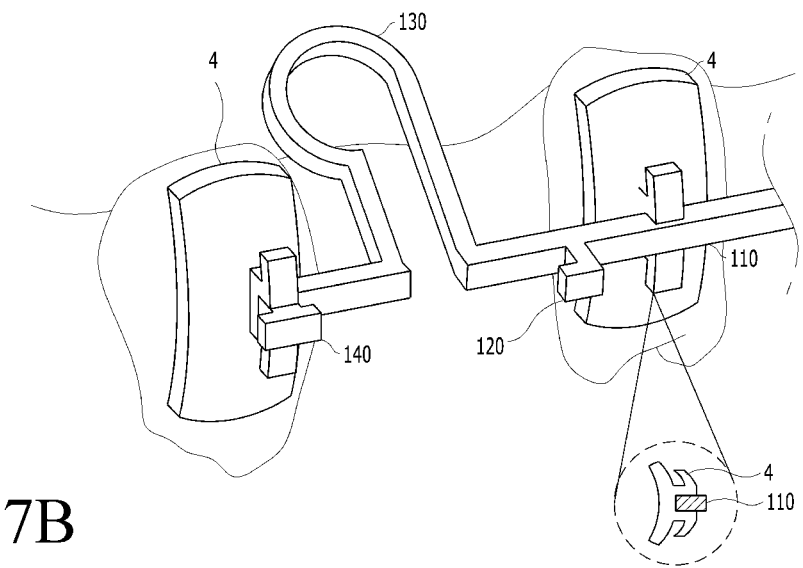

FIGS. 7A and 7B show the state in which the archwire is ligated to the bracket after the tooth is extracted, and it can be recognized that the loop 130 is positioned before the tooth extracting space.

Figure 5:
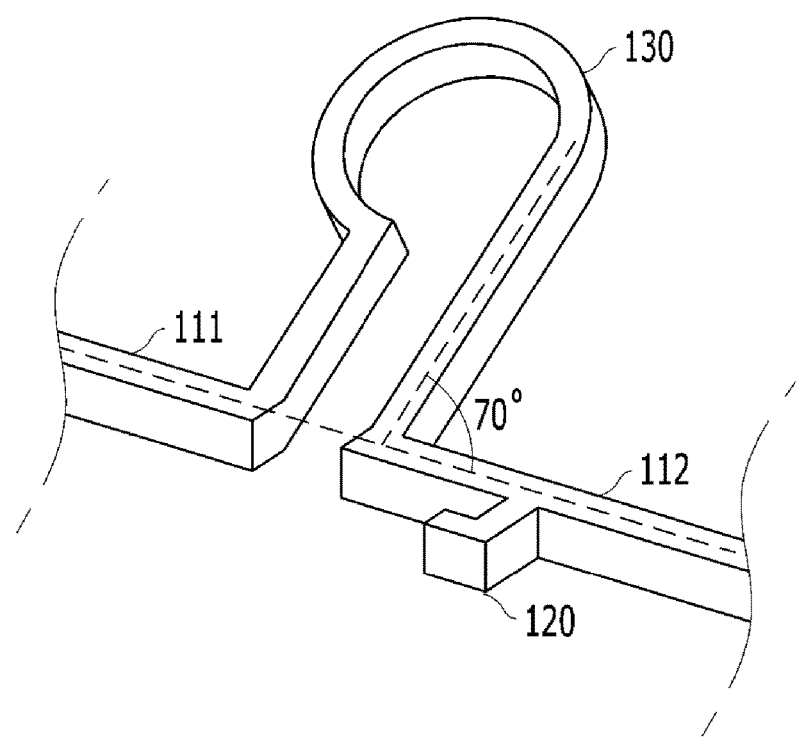
FIG. 5 is an enlarged view illustrating a loop and a hook of the archwire in FIG. 4.

FIG. 5 is an enlarged view illustrating the loop and the hook of the archwire in FIG. 4.

Referring to FIG. 5, the archwire body 110 includes a rectangular cross-sectional structure, and the hook 120 and the loop 130 protrude from any one side among four sides of the archwire body 110.

The hook 120 is arranged to be flush with the archwire body 110, but the loop 130 is bent upwardly at an angle of about 70 to 90 degrees.

Figure 6A:
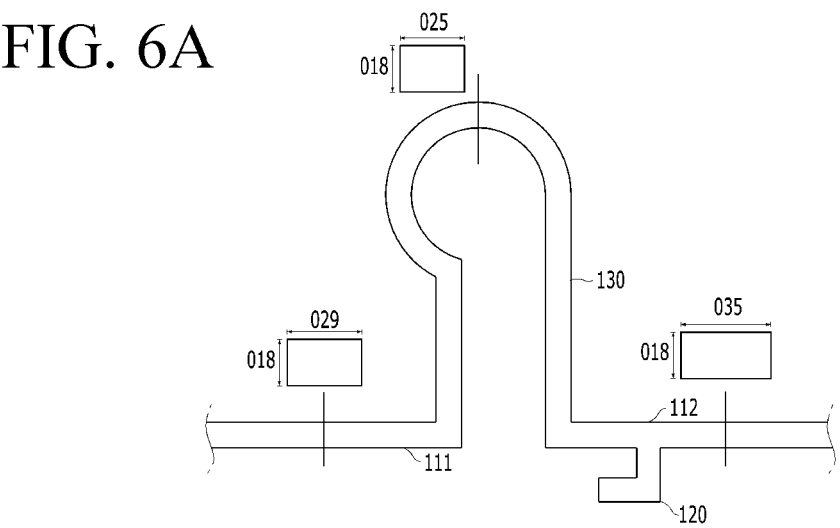
FIGS. 6A and 6B are enlarged views illustrating a process of fabricating the archwire in FIG. 4 and a cross-sectional structure thereof
Figure 6B:
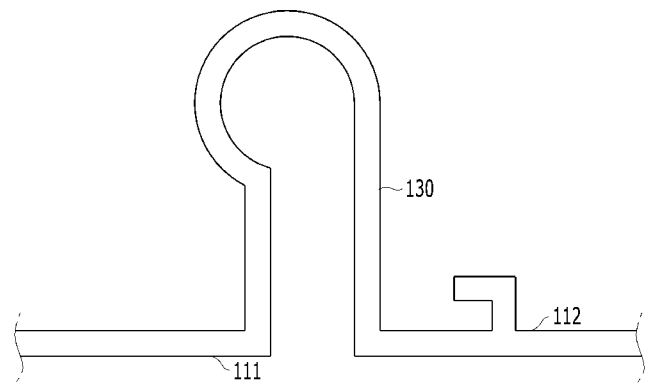

A process of fabricating the archwire with the varied cross section which is formed integrally with the hooks according to the embodiment of the present invention will be more clearly understood from FIGS. 6A and 6B.

FIGS. 6A and 6B show the shape of the archwire which is fabricated by shaping a plate of 0.18 inch in thickness.

First, a setup model of a patient is made, and then is converted into 3D data, thereby setting a location of a bracket for each tooth.

The location of the loop 130 is determined according to coordinates of the tooth extracting space. A kind of the loop 130 can be selected at this time.

The example in FIGS. 6A and 6B is showed in the shape of a delta loop, but various shapes of loops can be used.

FIGS. 8A and 8B illustrate examples of loops which can be applied to the present invention and cannot be applied to the present invention.

FIG. 8A shows the loops including a bull loop, an open vertical loop, an omega loop, and a key hole loop, in order from the left in the figure, as well as the delta loop in FIGS. 4 to 6, which can be applied to the present invention.

After the kind of the loop is determined, a height, a width and a thickness of the loop can be adjusted in order to impart a retraction force to the teeth when the wire is activated by 1 mm to 1.5 mm.

The adjustment of the height, the width and the thickness can be determined by simulation using dedicated software, in view of a space in an oral cavity of the patient.

If a sufficient force cannot be obtained due to the narrow space, it can be compensated by increasing the thickness of the loop.

Since an orthodontic wire of the related art is formed by manually bending a wire fabricated by a drawing method, it is not possible to adjust the thickness of the loop. The present invention can achieve the retraction force by adjusting the height or the thickness of the loop, while the width of the loop remains intact.

After the kind, the height and the thickness of the loop 130 are determined, the location and the kind of the hook 120 are set. Preferably, the hook 120 is set to have a width equal to or smaller than a width of a slot of the bracket 4.

Preferably, an interval between the hook 120 and the loop 130 is set within the range of 2 mm.

Since a common interval between the brackets is about 4 mm, the interval between the hook 120 and the loop 130 is designed not to exceed the half thereof.

The orientation of the hook 120 can be changed according to the lingual orthodontic treatment or the buccolingual orthodontic treatment, and also can be changed according to the bending direction, i.e., inward bending or outward bending, of the loop 130.

After the location of the bracket is determined on the basis of the setup model of the patient, the shape of the archwire body 110 is derived therefrom. Then, locations, sizes and kinds of the hooks 120 and the loops 130 provided on the archwire body 110 are determined according to the tooth extraction and the location of the tooth extraction, and the shape as shown in FIGS. 6A and 6B is shaped from a plate by electric discharge machining or laser machining.

Finally, the customized archwire is fabricated, as illustrated in FIG. 4, by bending the loop 130 in FIG. 5.

Since the archwire with the varied cross section which is formed integrally with the hooks according to the present invention has the cross-sectional shape varied along the region, as well as having the loops and stops which are formed integrally with the wire, the archwire cannot be fabricated by the drawing or extrusion method, but can be fabricated by the electric discharge machining or the laser machining.

Therefore, a material or a fabricating process should be considered.

A titanium molybdenum alloy (TMA) among materials for the orthodontic wires according to the related art is suitable for other materials, but there is a drawback in that frictional resistance is high when retracting the teeth.

Preferably, Ti6Al4V-ELI which is a kind of titanium alloys can be used in order to solve the above problem of the high frictional resistance, as well as being capable of being shaped from a plate.

Ti6Al4V-ELI is not used as a material for the orthodontic wire. However, it is proved that the material is suitable for the orthodontic archwire with the varied cross-sectional structure according to the present invention, because of the easy machining and the high compatibility with a human body.

Ti6Al4V-ELI has stiffness of about 0.56, which corresponds to a middle level between Nitinol of 0.17 and stainless steel of 1.

Preferably, the archwire with the varied cross section which is formed integrally with the hooks according to the present invention can be fabricated by forming a metal plate made of Ti6Al4V-ELI having a desired thickness (e.g., 0.018 inch). Since the loop 130 is not formed by manually bending the wire, it cannot be applied to an overlapped loop (multi-loop).

For example, the kinds of loops illustrated in FIG. 8B cannot be applied to the present invention.

FIG. 8B shows the loops including a closed helix loop, a double-delta closing loop, a closed horizontal loop, and closed T loop in order from the left in the figure.

Any loop which is not overlapped and can be fabricated by forming the plate can be applied to the archwire with the varied cross section which is formed integrally with the hooks according to the present invention. However, if there is an overlapped region, it cannot be applied to the present invention.

FIGS. 7A and 7B show the archwire according to the embodiment which is ligated to the slot of the bracket and is activated.

FIGS. 7A and 7B illustrate the state in which the archwire with the varied cross section which is formed integrally with the hooks according to the present invention is ligated to the brackets 4, and it can be recognized that the loop 130 is positioned in front of the tooth extracting region.

As illustrated in the enlarged views of FIGS. 7A and 7B, the archwire body 110 has a height of 0.018 inch which is equal to that of the slot of the bracket 4, and a width which is equal to or slightly larger than that of the slot of the bracket 4.

For example, the archwire body 110 can have the width of 0.029 inch or 0.035 inch along the region, as illustrated in FIGS. 6A and 6B.

The hook 120 has a height of 0.018 inch which is equal to that of the slot of the bracket 4, so that the hook 120 does not abut against the slot of the bracket 4 for molar teeth in the process of retracting the anterior teeth.

The loop 120 and the hook 130 can be formed to have a sufficient small size, thereby solving a problem in that whenever the teeth are retracted by about 1 to 2 mm, the hook should be detached and mounted onto the wire.

Also, the archwire with the varied cross section which is formed integrally with the hooks according to the present invention may include a stop 140 protruding from one side of the archwire body 110, as illustrated in FIGS. 7A and 7B.

The stop 140 may further protrude from the slot of the bracket, as the archwire body 110 is ligated to the slot of the bracket.

The portion protruding from the slot may be formed of a T-shape, as illustrated in FIGS. 7A and 7B.

The stop 140 may be provided at a positon corresponding to the slot of the bracket for central incisor, lateral incisor or canine so as to further protrude from the slot of interest. One or more stops may be provided on the wire.

The stop 140 is fixed by a ligating wire, as illustrated in FIGS. 7A and 7B, and serves to limit horizontally sliding movement of the archwire body 110 in the slot of the bracket.

The stop 140 is formed integrally with the archwire body 110.

Referring back to FIGS. 6A and 6B, the design of the cross section to improve conformance of the archwire will now be described.

The archwire in FIGS. 4 to 7 is customized for the lingual orthodontic treatment. In order to maintain the retraction force at the lingual orthodontic treatment which is limited to the narrow space and also provide the wire with proper resilience, the portion ligated to the slot of the bracket 4 has the same size (e.g., 0.018 inch in height and 0.025 inch in width) as that of the slot so that the portion can be interference-fitted into the slot. However, it is possible to allow the cross-sectional area of the region between the brackets to have the size smaller than the above size.

For example, the width of the inter-bracket region can be set to 0.018 inch, while the height is fixed to 0.018 inch.

The wire can be designed to have the above size since the bracket ligating position can be figured out in advance through the setup model of the patient.

The archwire body 110 may be formed such that an anterior wire region 111 and a posterior wire region 112 have a different cross-sectional area on the basis of the loop 130.

For example, as illustrated in FIGS. 6A and 6B, the cross-sectional area of the posterior wire region 112 can be increased by setting the width of the anterior wire region 111 to 0.029 inch and the width of the posterior wire region 112 to 0.035 inch while the height is fixed to 0.018 inch.

If a rear portion of the loop 130 is extended, the loop may not support the force and thus be bent.

It is known that a load deflection rate of the wire with a loop formed thereon is in inverse proportion to a cube of a length.

By increasing the cross-sectional area of the posterior wire region 112 which is positioned at the rear of the anterior wire region 112 corresponding to the front of the loop 130, it is possible to prevent the rear portion of the loop 130 from being bent.

Now, the configuration of an archwire with a varied cross section which is formed integrally with hooks according to another embodiment of the present invention will be described with reference to FIGS. 9 to 11.

According to this embodiment, the archwire is formed integrally with the hook, and can be applied to the sliding technique.

Figure 9:
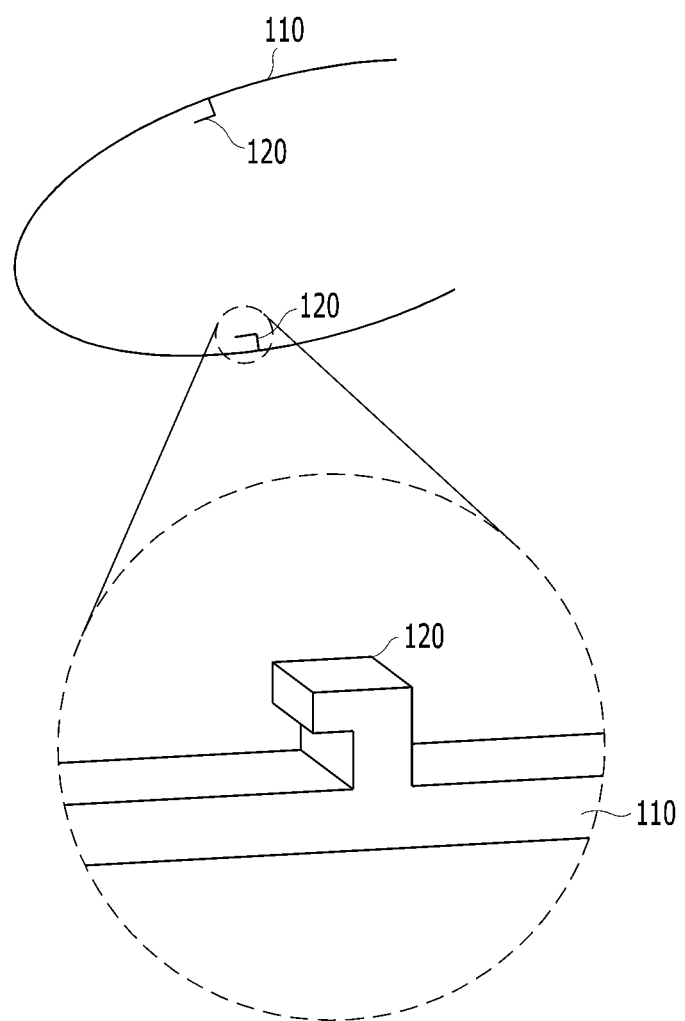
FIG. 9 is a view schematically illustrating an archwire with a varied cross section which is formed integrally with hooks according to another embodiment of the present invention.

FIG. 9 is a view schematically illustrating an archwire with a varied cross section which is formed integrally with hooks according to another embodiment of the present invention.

Referring to FIG. 9, the archwire body 110 is provided with the hook 120 on one side thereof The fabricating method and the material have been described above.

In order to improve the conformance of the retraction wire, the archwire body 110 may be divided into an anterior region and a posterior region.

Since a bonding location of each bracket can be figured out in advance from the setup model of the patient's teeth, the archwire body 110 is divided into a portion which is ligated to posterior brackets, and a portion which is ligated to anterior brackets.

The cross-sectional area of the posterior wire region 112 can be set to be larger than that of the anterior wire region 111.

With the above configuration, it is possible to impart the sufficient retraction force to the teeth when the central incisor is retracted in a rearward direction, and the resilience of the anterior wire region 111 can be maintained.

Figure 10:
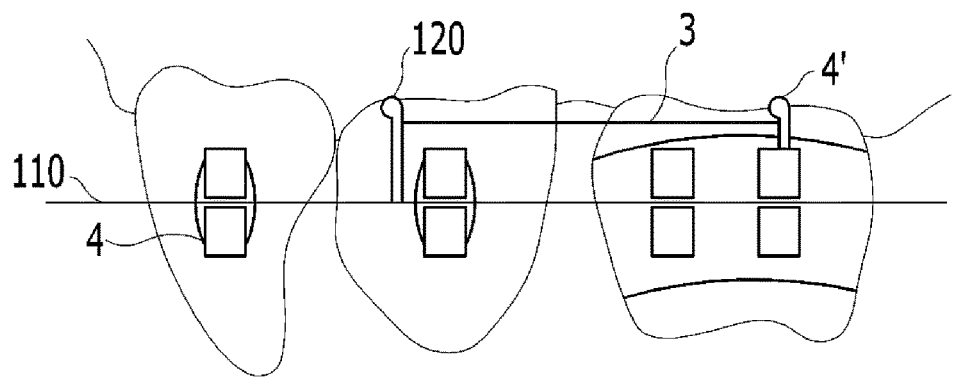
FIG. 10 is a view illustrating the archwire in FIG. 9 which is ligated to slots of brackets.

FIG. 10 is a view illustrating the archwire in FIG. 9 which is ligated to the slots of the brackets.

The hook 120 faces upward, contrary to the embodiment illustrated in FIGS. 7A and 7B. An angle or location of the hook 120 may be optionally selected, and the embodiment in FIG. 10 corresponds to an example of the hook 120 commonly used for the sliding technique.

FIGS. 11A, 11B, 11C and 11D are views of a modified embodiment of the hook.

The hook 120 is ligated and tightened with a ligating wire to activate the loop 130, and a shape or size of the hook is not limited.

Various shapes of hooks in FIGS. 11A, 11B, 11C and 11D can be used.

Figure 11A:
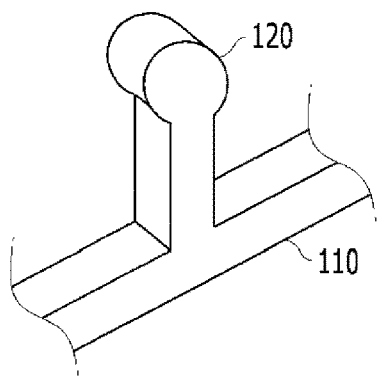
FIGS. 11A, 11B, 11C and 11D are views of a modified embodiment of the hook.
Figure 11B:
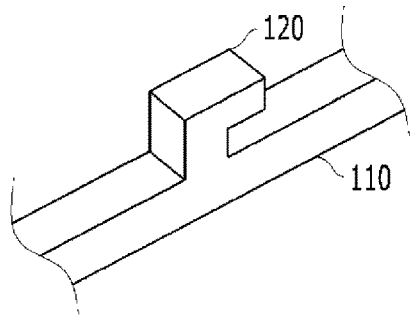
Figure 11C:
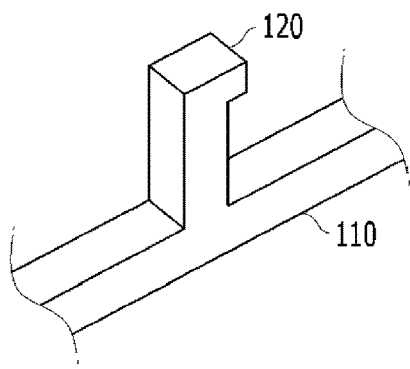
Figure 11D:
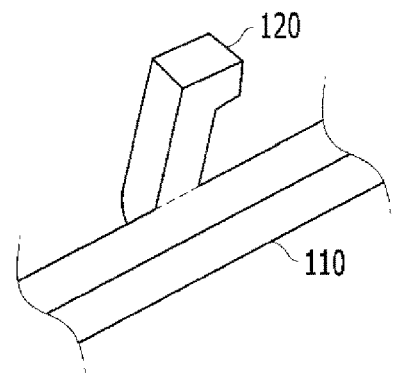

In particular, when the archwire is used for the sliding technique, the hook is bent, as illustrated in FIG. 11D, to minimize feeling of irritation and discomfort within the narrow space of the oral cavity.

The technical thoughts of the present invention have been described hereinafter.

It is to be appreciated that those skilled in the art can change or modify the embodiments from the above description.

Although it is not clearly illustrated or described herein, it is to be appreciated that those skilled in the art can change or modify the embodiments from the above description without departing from the scope and spirit of the present invention. While the present invention has been described with reference to the particular illustrative embodiments, it is not to be restricted by the embodiments but only by the appended claims.

What is claimed is:

1. An orthodontic appliance having an archwire with a variable cross section, comprising:
   brackets having slots and located in a position according to a setup model of a patient's teeth;
   an archwire having a body ligated to the slots of the brackets in such a way that at least one region of the body has a cross section different from that of another region thereof; and
   a hook, a loop, and a stop integrally formed with the body of the archwire,
   wherein a location and a kind of the loop are determined according to a tooth extraction location of the patient; the hook is disposed within a predetermined distance from the loop and has a height that is equal to or smaller than a height of the bracket slots; and the stop protrudes from the slot of a corresponding bracket ligated thereto.

2. The orthodontic appliance having an archwire with a variable cross section according to claim 1, wherein the hook and the stop are flush with each other.

3. The orthodontic appliance having an archwire with a variable cross section according to claim 1, wherein the archwire body is divided into a posterior wire region and an anterior wire region, and a cross-sectional area of the posterior wire region is larger than that of the anterior wire region.

4. The orthodontic appliance having an archwire with a variable cross section according to claim 1, wherein a cross-sectional area of the archwire body at the loop is variably determined corresponding to the setup model of the patient's teeth.

* * * * *